United States Patent [19]

Yagihara et al.

[11] 4,367,282

[45] Jan. 4, 1983

[54] SILVER HALIDE COLOR PHOTOGRAPHIC LIGHT-SENSITIVE MATERIAL

[75] Inventors: Morio Yagihara; Tsumoru Hirano; Keiji Mihayashi, all of Minami-ashigara, Japan

[73] Assignee: Fuji Photo Film Co., Ltd., Kanagawa, Japan

[21] Appl. No.: 328,151

[22] Filed: Dec. 7, 1981

[30] Foreign Application Priority Data

Dec. 5, 1980 [JP] Japan ................................ 55/171544

[51] Int. Cl.$^3$ .......................... G03C 7/00; G03C 1/40
[52] U.S. Cl. ..................... 430/381; 430/387; 430/548; 430/555; 430/558; 430/549
[58] Field of Search ............... 430/381, 387, 548, 555, 430/558

[56] References Cited

U.S. PATENT DOCUMENTS

| | | | |
|---|---|---|---|
| 3,926,436 | 12/1975 | Monbaliu et al. | 430/548 |
| 4,076,533 | 2/1978 | Ota et al. | 430/558 |
| 4,080,211 | 3/1978 | Van Paesschen et al. | 430/548 |
| 4,128,427 | 12/1978 | Monbaliu et al. | 430/548 |
| 4,241,168 | 12/1980 | Arai et al. | 430/555 |
| 4,301,235 | 11/1981 | Ichijima et al. | 430/387 |
| 4,310,619 | 1/1982 | Ichijima et al. | 430/387 |

*Primary Examiner*—J. Travis Brown
*Attorney, Agent, or Firm*—Sughrue, Mion, Zinn, Macpeak & Seas

[57] ABSTRACT

A silver halide color photographic light-sensitive material is described comprising a support having thereon a silver halide emulsion layer containing a 2-equivalent magenta color image forming polymer coupler latex which is capable of forming a dye upon coupling with an oxidation product of an aromatic primary amine developing agent and which is a polymer or copolymer having a repeating unit derived from a monomer represented by formula (I)

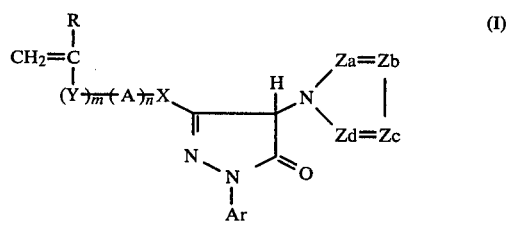

wherein R represents a hydrogen atom, a lower alkyl group containing from 1 to 4 carbon atoms or a chlorine atom; X represents —CONH—, —NH—, —NHCONH— or —NHCOO—; Y represents —CONH— or —COO—; A represents an unsubstituted or substituted alkylene group which may be a straight chain or a branched chain or an unsubstituted or substituted phenylene group; Ar represents an unsubstituted or substituted phenyl group; Za, Zb, Zc and Zd can each represent a methine group, a substituted methine group or -N=; m represents 0 or 1; and n represents 0 or 1.

The 2-equivalent magenta color image forming polymer coupler latex has a good color forming property and is capable of forming a dye with a high yield and without formation of undesired stains and fogs and provides a stable magenta image having a good fastness to light, heat, and humidity. A method of forming a color image using the silver halide color photographic light-sensitive material is also described.

15 Claims, No Drawings

SILVER HALIDE COLOR PHOTOGRAPHIC LIGHT-SENSITIVE MATERIAL

FIELD OF THE INVENTION

The present invention relates to a silver halide color photographic light-sensitive material containing a novel 2-equivalent magenta color image forming polymer coupler latex capable of coupling with an oxidation product of an aromatic primary amine developing agent.

BACKGROUND OF THE INVENTION

It is well known that for the color development of a silver halide photographic light-sensitive material, after exposure, an oxidized aromatic primary amine developing agent can be reacted with a dye forming coupler to obtain a color image.

It is also known that, for the color development of a silver halide color photographic material, an oxidized aromatic primary amine color developing agent can be reacted with a coupler to form a dye such as an indophenol, an indoaniline, an indamine, an azomethine, a phenoxazine, a phenazine, and the like, thus forming a color image. In this procedure, the subtractive color process is ordinarily used for color reproduction, and silver halide emulsions which are selectively sensitive to blue, green, and red light, and yellow, magenta, and cyan color image formers, which are respectively the complementary colors of blue, green, and red, are employed. For example, a coupler of the acylacetanilide or benzoylmethane type is used for forming a yellow color image; a coupler of the pyrazolone, pyrazolobenzimidazole, cyanoacetophenone or indazolone type is generally used for forming a magenta color image; and a phenolic coupler, such as a phenol and a naphthol, is generally used for forming a cyan color image.

It is also known that, in addition to color couplers which do not have a substituent at the coupling position thereof, and thus require development of 4 mols of exposed silver halide for forming 1 mol of a dye, there are color couplers which have a substituent capable of being released upon color development at the coupling position thereof, and thus require development of only 2 mols of exposed silver halide for forming 1 mol of a dye. The former are known as 4-equivalent couplers, and the latter are known as 2-equivalent couplers.

Color couplers must satisfy various requirements. For example, it is necessary that they have a good spectral property and provide a dye image having excellent stability to light, temperature, and humidity for a long period of time upon color development.

It is also required in a multilayer color photographic light-sensitive material that each coupler is fixed in a layer separated from each other in order to reduce color mixing and to improve color reproduction. Many methods for rendering a coupler diffusion-resistant are known. One method is to introduce a long chain aliphatic group into a coupler molecule in order to prevent diffusion. Couplers according to such a method require a step of addition to an aqueous gelatin solution by solubilizing in alkali, or a step of dispersing in an aqueous gelatin solution by dissolving in a high boiling organic solvent, since the couplers are immiscible with an aqueous gelatin solution.

Another method for rendering a coupler diffusion-resistant is to utilize a polymer coupler obtained by polymerization of a monomeric coupler. However, such polymer couplers have disadvantages, in that they have poor solubility to water, and they increase the viscosity of an aqueous gelatin solution. In order to overcome these disadvantages, polymer coupler latexes have been provided. The method of adding a polymer coupler in a latex form to a hydrophilic colloid composition has many advantages in comparison with other methods. For example, when the polymer coupler latex is used, the step of adding the coupler to a coating solution can be simplified, since the use of a high boiling organic solvent or an alkali is not necessary and a special dispersing method is not required. Further, the deterioration of strength of the film formed is small, because the hydrophobic substance is in a latex form. Also, the thickness of the layer can be reduced, since an organic solvent is not contained therein. Furthermore, since the latex can contain coupler monomers in a high concentration, it is easy to incorporate couplers in a high concentration into a photographic emulsion, and the increase of viscosity is small. Moreover, the crystallization of couplers in the emulsion layer is also prevented thereby.

As a polymer coupler latex described above, for example, a 4-equivalent magenta polymer coupler latex and method of preparation thereof are disclosed in U.S. Pat. No. 4,080,211 and British Pat. No. 1,247,688, a copolymer latex of a competing coupler in West German Pat. No. 2,725,591 and U.S. Pat. No. 3,926,436, and cyan polymer coupler latex in U.S. Pat. No. 3,767,412.

However, these polymer coupler latexes have a number of problems in addition to the many advantages described above, and thus it has been desired to overcome these problems. The problems include the following:

1. The rate of the coupling reaction is poor, and thus the density of dye formed is very low.
2. The light fastness of the magenta color image is very poor.
3. Undesirable fog is readily formed upon color development.
4. The fastness to humidity and heat of the color image is poor.
5. The latexes cannot be stored for a long time since aggregation thereof occurs in solution.
6. The resistance to formalin is very poor.

More particularly, they have major disadvantages in coupling reactivity, resistance to formalin, and light fastness. With respect to the coupling reactivity, no improvement is obtained by using the 2-equivalent magenta polymer coupler latex described in West German Pat. No. 2,725,591 and U.S. Pat. No. 3,926,436. This suggests that there are great differences in photographic properties between conventional couplers and polymer couplers.

SUMMARY OF THE INVENTION

Therefore, an object of the present invention is to provide a novel 2-equivalent magenta color image forming polymer coupler latex in which the disadvantages described above are overcome, and which has an excellent color forming property.

Another object of the present invention is to provide a novel 2-equivalent magenta color image forming polymer coupler latex which is capable of forming a dye in a high yield and without the formation of undesirable fog and stain.

Another object of the present invention is to provide a 2-equivalent magenta color image forming polymer coupler latex which shows an improved conversion rate to dye and an improved resistance to decreases in color forming properties upon the attack of chemical substances.

Still another object of the present invention is to provide a color photographic light-sensitive material that forms a color image fast to light, heat, and humidity and heat in a color photograph after development processing.

A further object of the present invention is to provide a color photographic light-sensitive material having good film strength.

A further object of the present invention is to provide a color photographic light-sensitive material having a reduced layer thickness and an improved sharpness.

A still further object of the present invention is to provide a method of forming a magenta color image by development of a silver halide emulsion in the presence of a novel 2-equivalent polymer coupler latex.

A still further object of the present invention is to provide a silver halide color photographic light-sensitive material containing a novel 2-equivalent magenta color image forming polymer coupler latex, a photographic processing method or an image forming method using thereof.

Other objects of the present invention will be apparent from the following detailed description and examples.

As a result of extensive investigations, it has now been found that these objects of the present invention are accomplished by the use of a 2-equivalent magenta color image forming polymer coupler latex which is a polymer or copolymer having a repeating unit derived from a monomer represented by formula (I)

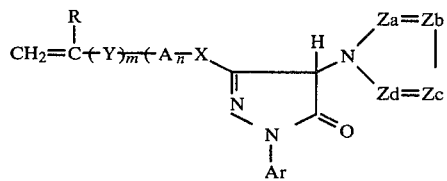
(I)

wherein R represents a hydrogen atom, a lower alkyl group containing from 1 to 4 carbon atoms, or a chlorine atom; X represents —CONH—, —NH—, —NHCONH— or —NHCOO—; Y represents —CONH— or —COO—; A represents an unsubstituted or substituted alkylene group which may be a straight chain or a branched chain or an unsubstituted or substituted phenylene group; Ar represents an unsubstituted or substituted phenyl group; Za, Zb, Zc, and Zd (which may be the same or different) can each represent a methine group, a substituted methine group or —N=; m represents 0 or 1; and n represents 0 or 1.

In more detail, the objects of the invention can be accomplished with a color photographic light-sensitive material comprising a support having thereon at least one silver halide emulsion layer containing a 2-equivalent magenta color image forming polymer coupler latex which is a novel homopolymer having a repeating unit represented by formula (II) described below, or a novel copolymer of the repeating unit described below and a non-color forming unit which does not couple with the oxidation product of an aromatic primary amine developing agent.

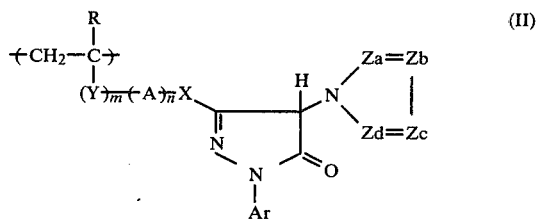
(II)

In formula (II), R, X, Y, A, Ar, Za, Zb, Zc, Zd, m and n have the same meanings as in the case of formula (I)

DETAILED DESCRIPTION OF THE INVENTION

The novel 2-equivalent magenta color image forming polymer coupler latex according to the present invention includes a polymer having a repeating unit derived from a monomer coupler represented by formula (I), and a copolymer of the repeating unit according to formula (II) and at least one non-color forming unit containing at least one ethylene group which does not have an ability of oxidative coupling with an aromatic primary amine developing agent.

In the above-described formula (I), R represents a hydrogen atom, a lower alkyl group having from 1 to 4 carbon atoms, or a chlorine atom; X represents —CONH—, —NH—, —NHCONH—, or —NHCOO—; Y represents —CONH— or —COO—; A represents an unsubstituted or substituted alkylene group, preferably having from 1 to 10 carbon atoms, which may be a straight chain or a branched chain (for example, a methylene group, a methylmethylene group, a dimethylmethylene group, a dimethylene group, a trimethylene group, a decylmethylene group, etc.) or an unsubstituted or substituted phenylene group.

Substituents for the alkylene group or the phenylene group represented by A include an aryl group (for example, a phenyl group, etc.), a nitro group, a hydroxy group, a cyano group, a sulfo group, an alkoxy group (for example, a methoxy group, etc.), an aryloxy group (for example, a phenoxy group, etc.), an acyloxy group (for example, an acetoxy group, etc.), an acylamino group (for example, an acetylamino group, etc.), a sulfonamido group (for example, a methanesulfonamido group, etc.), a sulfamoyl group (for example, a methylsulfamoyl group, etc.), a halogen atom (for example, a fluorine atom, a chlorine atom, a bromine atom, etc.), a carboxy group, a carbamoyl group (for example, a methylcarbamoyl group, etc.), an alkoxycarbonyl group (for example, a methoxycarbonyl group, etc.), a sulfonyl group (for example, a methylsulfonyl group, etc.), and the like. When two or more substituents are present, they may be the same or different.

Ar represents an unsubstituted or substituted phenyl group. Substituents for the phenyl group include an alkyl group (for example, a methyl group, an ethyl group, etc.), an alkoxy group (for example, a methoxy group, an ethoxy group, etc.), an aryloxy group (for example, a phenoxy group, etc.), an alkoxycarbonyl group (for example, a methoxycarbonyl group, etc.), an acylamino group (for example, an acetylamino group, etc.), a carbamoyl group, an alkylcarbamoyl group (for example, a methylcarbamoyl group, an ethylcarbamoyl group, etc.), a dialkylcarbamoyl group (for example, a dimethylcarbamoyl group, etc.), an arylcarbamoyl group (for example, a phenylcarbamoyl group, etc.), an alkylsulfonyl group (for example, a methylsulfonyl group, etc.), an arylsulfonyl group (for example, a phenylsulfonyl group, etc.), an alkylsulfonamido group (for example, a methanesulfonamido group, etc.), an arylsulfonamido group (for example, a phenylsulfonamido group, etc.), a sulfamoyl group, an alkylsulfamoyl group (for example, an ethylsulfamoyl group, etc.), a dialkylsulfamoyl group (for example, a dimethylsulfamoyl group, etc.), an alkylthio group (for example, a methylthio group, etc.), an arylthio group (for example, a phenylthio group, etc.), a cyano group, a nitro group, a halogen atom (for example, a fluorine atom, a chlorine atom, a bromine atom, etc.), and the like. When two or more substituents are present, they may be the same or different.

Particularly preferred substituents include a halogen atom, an alkyl group, an alkoxy group, an alkoxycarbonyl group and a cyano group.

The group connected at the 4-position of the 5-pyrazolone ring in formula (I) is partially represented, in detail, by formula (III)

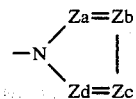  (III)

wherein Za, Zb, Zc, and Zd (which may be the same or different) each represents an unsubstituted methine group, a substituted methine group (for example, a methine group substituted with a straight chain or branched chain alkyl group having from 1 to 10 carbon atoms, a cycloalkyl group, an aralkyl group, an aryl group or a heterocyclic group, and further a methine group substituted with an alkoxycarbonyl group, an aryloxycarbonyl group, an aralkyloxycarbonyl group, an alkoxy group, an aryloxy group, an alkylthio group, a carboxy group, an acylamino group, a diacylamino group, an N-alkylacylamino group, an N-arylacylamino group, a ureido group, a thioureido group, an alkyloxycarbonylamino group, an aryloxycarbonylamino group, an anilino group, an alkylamino group, a cycloamino group, an alkylcarbonyl group, an arylcarbonyl group, a sulfonamido group, a carbamoyl group, a sulfamoyl group, a cyano group, an acyloxy group, a sulfonyloxy group, an alkylsulfonyl group, an arylsulfonyl group, a halogen atom, a sulfo group or a nitro group), or —N=.

Specific examples of nitrogen containing heterocyclic groups formed by Za, Zb, Zc, Zd and —N> according to formula (III) and released upon coupling with the oxidation product of an aromatic primary amine developing agent include a pyrazolyl group, an imidazolyl group, a triazolyl group, a tetrazolyl group, etc. Of these groups, a pyrazolyl group in which Za represents —N= and Zb, Zc, and Zd each represents a methine group or a substituted methine group (the substituents for the substituted methine group being the same as those described above) is particularly preferred.

The substituted methine groups represented by Za, Zb, Zc, and Zd may be two or more, and the substituents may be bonded to each other to form a ring.

m represents 0 or 1, and n represents 0 or 1.

Examples of the non-color forming monomer which does not couple with the oxidation product of an aromatic primary amine developing agent include an ester, preferably a lower alkyl ester and an amide, derived from an acrylic acid, for example, an acrylic acid, an α-chloroacrylic acid, an α-alkylacrylic acid such as a methacrylic acid, for example, acrylamide, methacrylamide, t-butylacrylamide, methyl acrylate, ethyl acrylate, n-propyl acrylate, n-butyl acrylate, 2-ethylhexyl acrylate, n-hexyl acrylate, octyl methacrylate, lauryl methacrylate, etc., a vinyl ester, for example, vinyl acetate, vinyl propionate, vinyl laurate, etc., acrylonitrile, methacrylonitrile, an aromatic vinyl compound, for example, styrene and a derivative thereof, for example, vinyl toluene, divinyl benzene, vinyl acetophenone, sulfo styrene, etc., itaconic acid, citraconic acid, crotonic acid, vinylidene chloride, a vinyl alkyl ether, for example, vinyl ethyl ether, an ester of maleic acid, N-vinyl-2-pyrrolidone, N-vinyl pyridine, 2- or 4-vinyl pyridine, etc.

Two or more comonomer compounds described above can be used together with. For example, a combination of n-butyl acrylate and divinyl benzene, styrene and methacrylic acid, n-butyl acrylate and methacrylic acid, etc., can be used.

The ethylenically unsaturated monomer which is used to copolymerize with the monomer compound containing a 2-pyrazolin-5-one moiety and represented by above-described formula (I) can be selected so that the copolymer to be formed possesses good physical properties and/or chemical properties, for example, solubility, compatibility with a binder such as gelatin in a photographic colloid composition, flexibility, heat stability, etc.

The 2-equivalent magenta color image forming polymer coupler latex used in the present invention can be prepared by an emulsion polymerization method. Such methods for preparation of polymer coupler latexes in an aqueous medium are described, for example, in an aqueous gelatin phase in U.S. Pat. No. 3,370,952 and in water in U.S. Pat. No. 4,080,211. These methods can be applied to preparation of homopolymers and preparation of copolymers. In the latter case, comonomer is preferably a liquid comonomer which may act, in some cases, as a solvent for a monomer which is solid in normal state.

Preferred examples of emulsion polymerization initiators which can be used in the emulsion polymerization methods include a persulfate such as ammonium persulfate, potassium persulfate, etc., an azonitrile compound such as 4,4'-azo-bis(4-cyanovaleric acid), etc., a peroxide such as benzoyl peroxide, etc., hydrogen peroxide, etc.

As an emulsion polymerization aid, a compound having surface activity is used. Preferred examples include soap, a sulfonate, a sulfate, a cationic compound, an amphoteric compound, a polymeric protective colloid, etc.

It is desirable that a ratio of the color forming portion in the polymer latex is usually from 5 to 80% by weight. In this case, an equivalent molecular weight, that is, a gram number of the polymer containing 1 mol of a coupler monomer is preferably from about 250 to 3,000, but it is not limited thereto.

Specific examples of pyrazolyl groups, triazolyl groups, imidazolyl groups, and tetrazolyl groups which are preferred as the nitrogen containing heterocyclic groups represented by formula (III) are set forth below, but the present invention is not to be construed to be limited thereto.

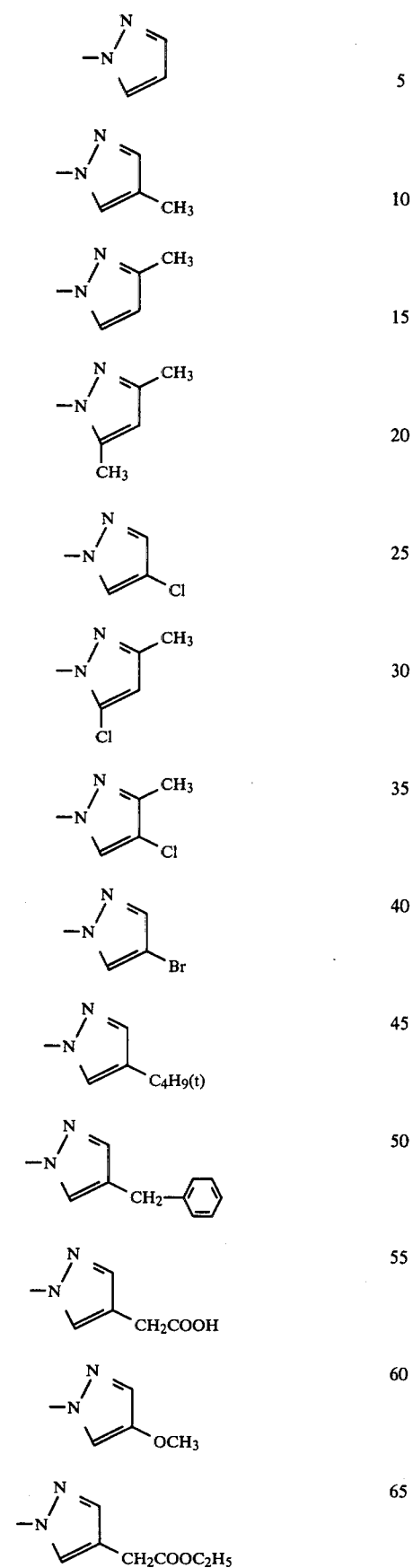
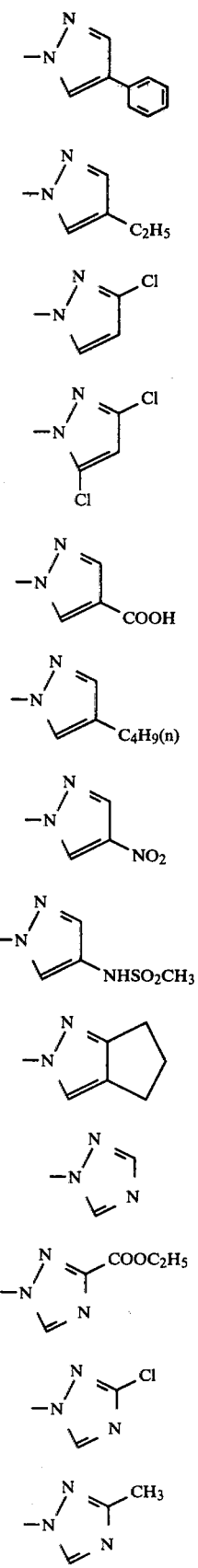

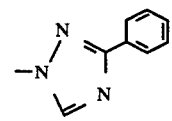
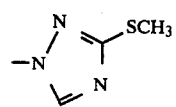
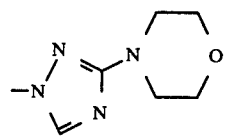
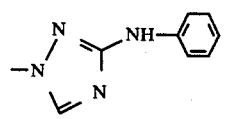
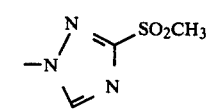
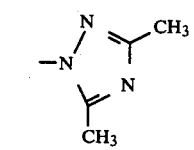
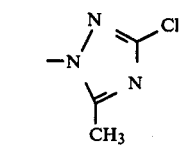
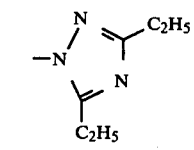
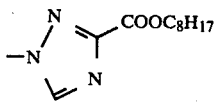
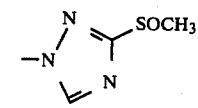
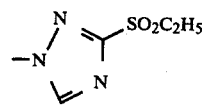
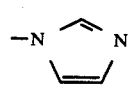
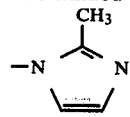
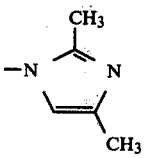
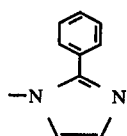
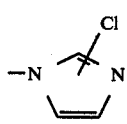
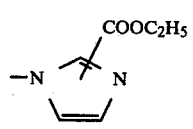
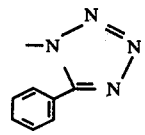
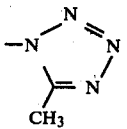
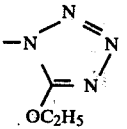
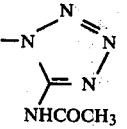
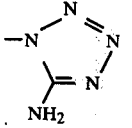
Preferred specific examples of monomers according to formula (I) used in the present invention are set forth below, but the present invention is not to be construed to be limited thereto.

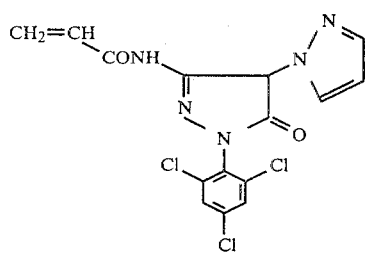 (1)
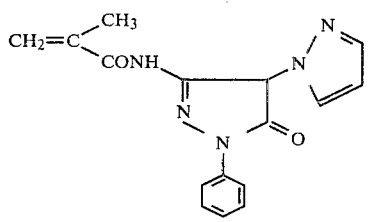 (2)
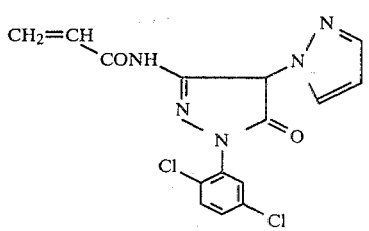 (3)
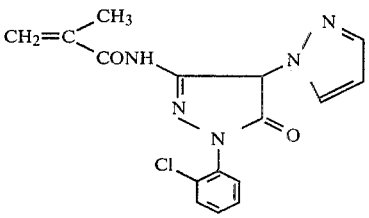 (4)
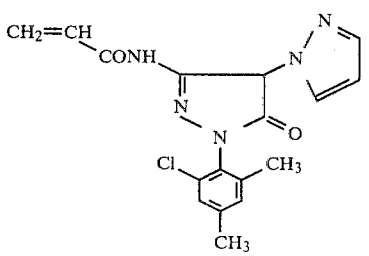 (5)
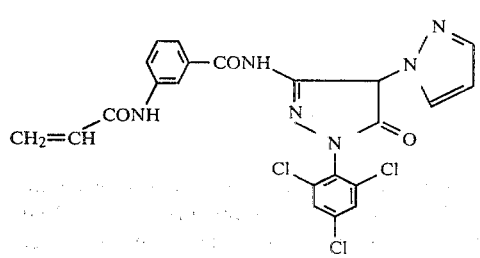 (6)
-continued
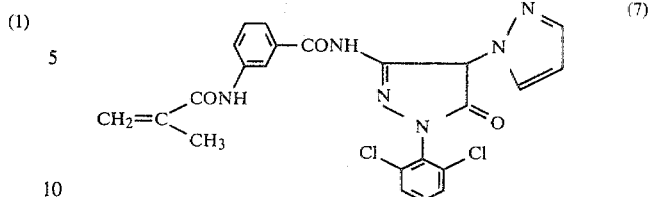 (7)
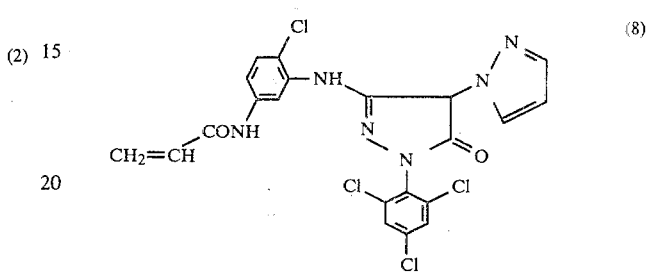 (8)
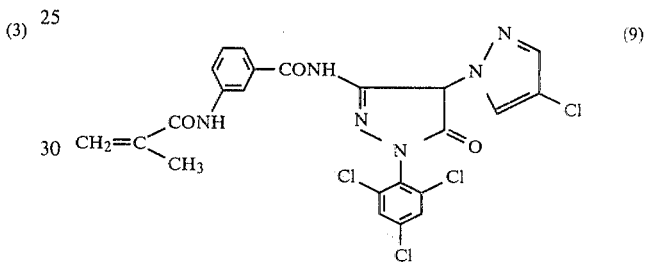 (9)
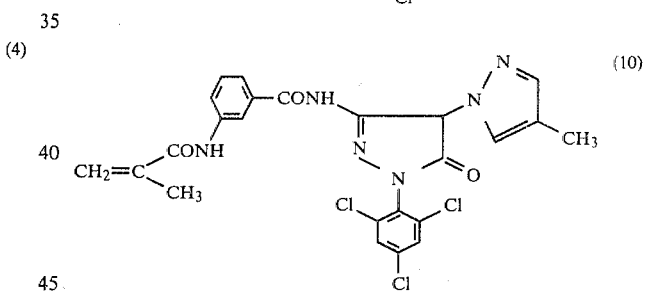 (10)
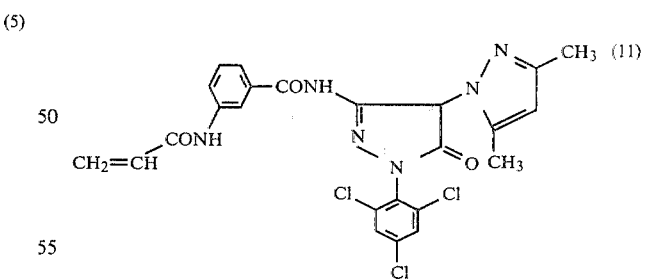 (11)
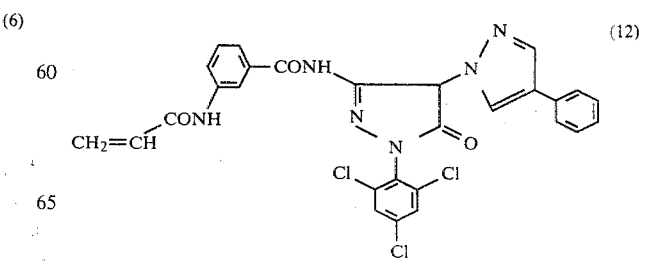 (12)

-continued
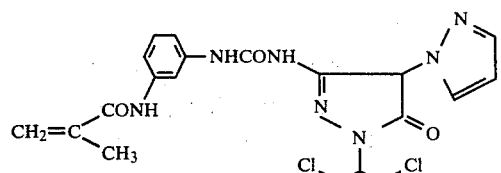 (13)
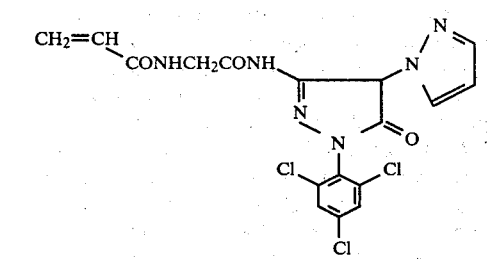 (14)
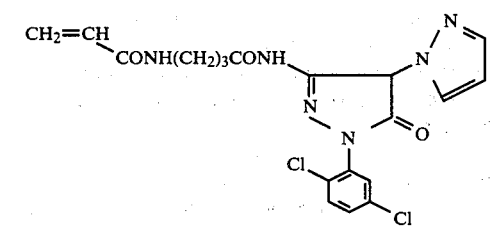 (15)
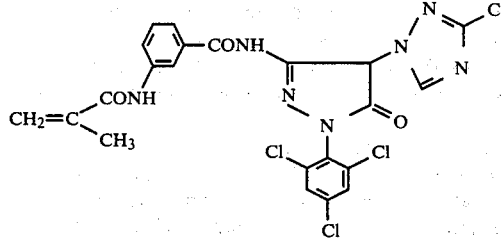 (16)
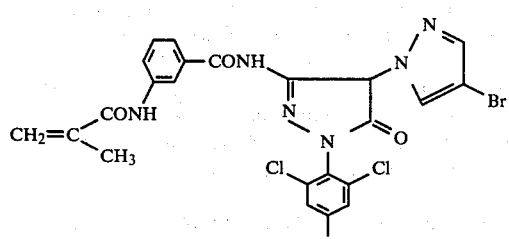 (17)
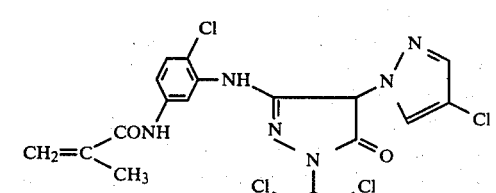 (18)
-continued
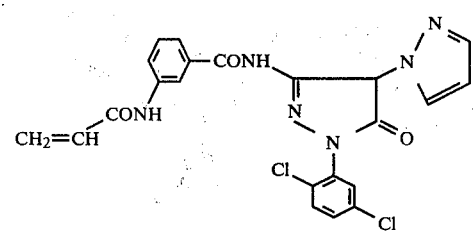 (19)
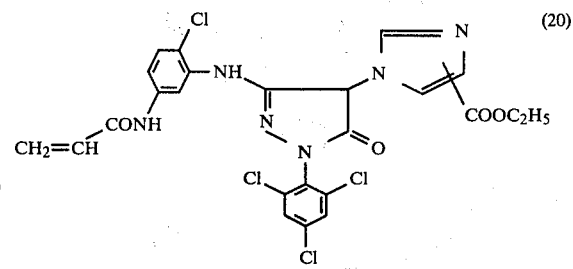 (20)
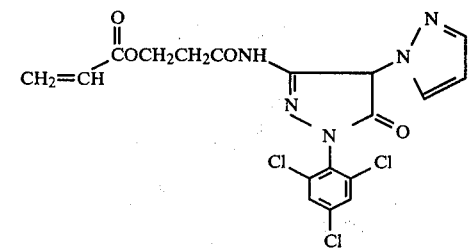 (21)
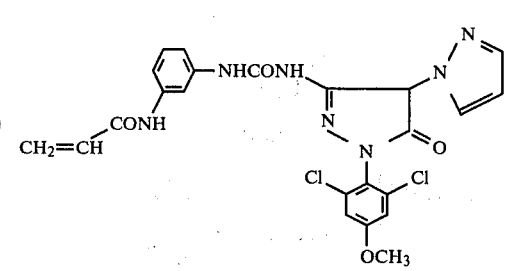 (22)
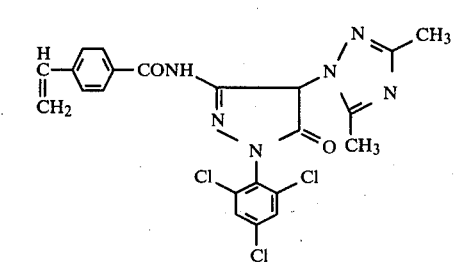 (23)
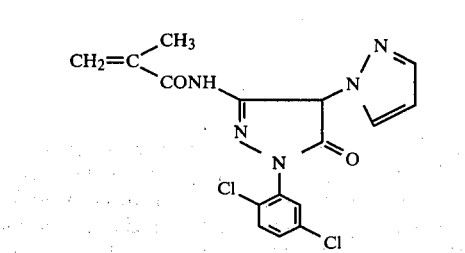 (24)

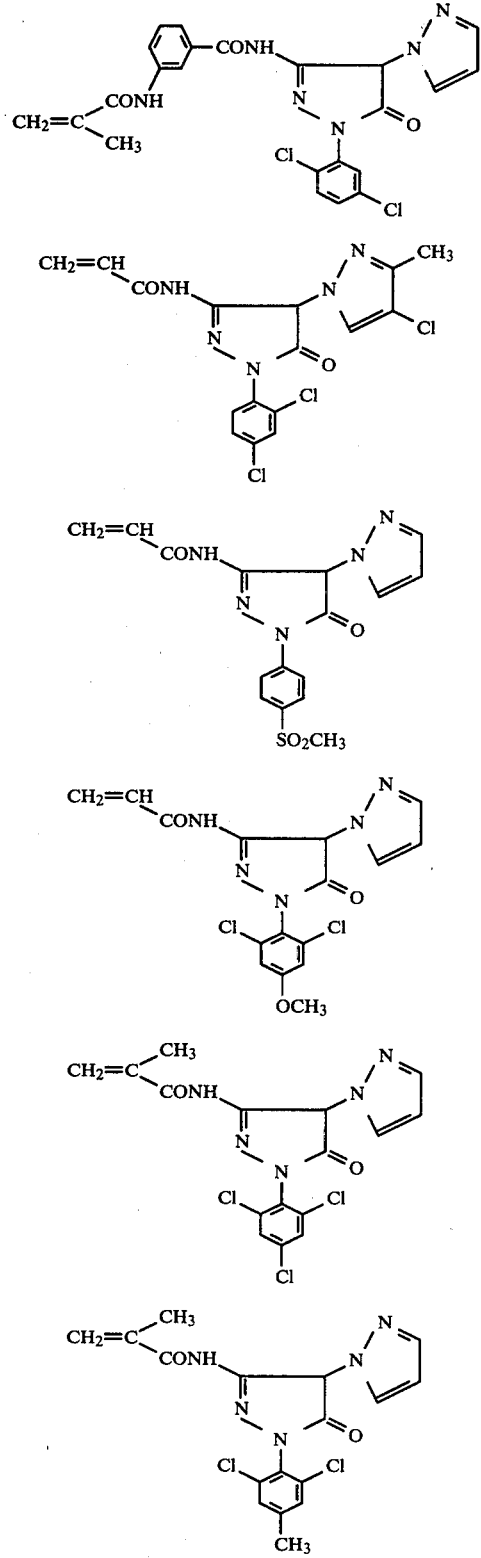

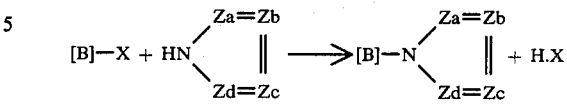

wherein [B] represents a magenta dye image forming residue, for example, a 4-pyrazolonyl group; Za, Zb, Zc and Zd each has the same meaning as defined hereinbefore; and X represents a halogen atom (for example, a chlorine atom, a bromine atom, etc.) substituted at the coupling position of a magenta coupler. With respect to the preparation of a 4-halogeno-5-pyrazolone, for example, in the case of a 5-pyrazolone ring, it can be synthesized by the methods described in U.S. Pat. Nos. 3,006,759 and 3,522,051. Also, in the special case in which an electron donative group such as an anilino group, etc., is substituted at the 3-position of the 5-pyrazolone ring, the mono-halogeno substituted compound can be easily synthesized by preparing a 3-N-alkoxycarbonylanilino-5-pyrazolone derivative or a 3-N-trichloroacetylanilino-5-pyrazolone and then halogenating the latter compound.

The synthesis procedure of the halogeno compound will be apparent in more detail in the synthesis examples described hereinafter.

The reaction of the thus-formed 4-halogeno-5-pyrazolone and a nitrogen containing aromatic heterocyclic compound can be carried out in a temperature range from 0° C. to 200° C., in various kinds of solvents, or in a fusion method without using a solvent. The preferred range of the temperature is from 20° C. to 150° C., and in the case of fusion method without solvent, it is not necessary to raise the temperature to more than the melting temperature at which both compounds melt.

Preferred examples of the solvents include an alcoholic solvent such as methanol, ethanol, propanol, etc., an aromatic solvent such as benzene, toluene, xylene, etc., an aprotic polar solvent such as dimethylformamide, hexamethylphosphoric triamide, etc., and the like.

In the reaction of a compound having an unpaired nitrogen electron in the ring thereof, for example, a diazole, a triazole, a tetrazole, etc., of the nitrogen containing aromatic heterocyclic compound with [B]-X, the heterocyclic compound can be used as a hydrogen halide-eliminating agent, and thus a base is not particularly required. However, the base can be used, if desired.

Of the nitrogen containing aromatic heterocyclic compounds, a pyrazole can be synthesized by methods as described in Justus Liebigs Annalen Der Chemie, Vol. 598, page 186 (1956), Naturewissenschaften, Vol. 44, page 442 (1957), Tetrahedron, Vol. 11, page 231 (1960), Zhur Obshcher Khim, Vol. 26, page 3355 (1956), The Journal of Organic Chemistry, Vol. 38, page 1777 (1973), ibid., Vol. 36, page 3081 (1971), ibid., Vol. 43, page 1367 (1978), Journal of the American Chemical Society, Vol. 78, page 2418 (1956), Journal of the Chemical Society, page 3259 (1958), etc.

An imidazole can be synthesized with reference to the methods described in The Chemistry of Heterocyclic Compounds, page 26 (Interscience, New York (1953)), J. Chem. Soc., page 1960 (1948), etc.

The coupler according to the present invention can generally be obtained by reacting a magenta coupler having a halogen atom at the coupling position with a nitrogen containing aromatic heterocyclic compound according to the following reaction equation as described in Japanese patent application (OPI) Nos. 20826/76, 58922/77 and 118034/80 (the term "OPI" as used herein refers to a "published unexamined Japanese patent application").

A triazole can be synthesized with reference to the methods described in *Chem. Pharm. Bull.*, Vol. 11, page 2871 (1976), *J. Medici. Chem.*, Vol. 21, page 1254 (1978), Japanese patent application (OPI) Nos. 36455/76, 31982/72, 19576/73 and 35165/75, etc.

Typical synthesis examples of the present invention are set forth below.

A. Monomer Compounds

SYNTHESIS EXAMPLE 1

Synthesis of 1-(2,4,6-trichlorophenyl)-3-(3-methacrylamidobenzamido)-4-pyrazolyl-5-oxo-2-pyrazoline [Coupler Monomer (7)]

428 g (1.0 mol) of 1-(2,4,6-trichlorophenyl)-3-(3-nitrobenzamido)-5-oxo-2-pyrazoline was added to 2.2 liters of dimethylformamide. To the solution, there was added dropwise 160 g (1.0 mol) of bromine with stirring while cooling with ice, and after stirring for about 1 hour, the reaction solution was poured into 9 liters of water. The crystals thus-separated were collected by filtration to obtain 489.5 g (96.6% yield) of 1-(2,4,6-trichlorophenyl)-3-(3-nitrobenzamido)-4-bromo-5-oxo-2-pyrazoline.

304 g (0.6 mol) of the 4-bromo compound thus-synthesized and 163 g (2.4 mols) of pyrazole were mixed well and reacted by heating at from about 80° C. to 90° C. under a nitrogen gas atmosphere for about 5 to 6 hours. After cooling to room temperature, 700 ml of acetonitrile was added to the reaction mixture and the crystals thus-separated were collected by filtration to obtain 197.5 g (66% yield) of 1-(2,4,6-trichlorophenyl)-3-(3-nitrobenzamido)-4-pyrazolyl-5-oxo-2-pyrazoline.

197.5 g (0.4 mol) of the 4-pyrazolyl compound thus-synthesized was added to 2 liters of methanol, to which a small amount of Raney nickel was added. To the mixture was gradually added dropwise 120 ml of hydrazine hydrate under heating with stirring and the mixture was reacted for about 1.5 hours. After removing the insoluble substance by filtration while hot, the filtrate was poured into water and the crystals thus-separated were collected by filtration followed by washing with methanol to obtain 127.2 g (68% yield) of 1-(2,4,6-trichlorophenyl)-3-(3-aminobenzamido)-4-pyrazolyl-5-oxo-2-pyrazoline.

Then, 39.5 g (0.08 mol) of the amino compound thus-synthesized was dissolved in 800 ml of tetrahydrofuran, to which were added 16 ml (0.2 mol) of pyridine and 2 ml of nitrobenzene. To the mixture there was further added dropwise 21 g (0.2 mol) of methacryloyl chloride while cooling with ice and the mixture was stirred for 1.5 hours. After adding 800 ml of water, the mixture was extracted with ethyl acetate and the extract was dried with anhydrous sodium sulfate. After distilling off the solvent under reduced pressure, the residual oily product was dissolved in 250 ml of ethanol, to which was then added an aqueous solution containing 4.8 g (0.12 mol) of sodium hydroxide dissolved in 100 ml of water at room temperature. After stirring for 30 minutes, 5 ml of acetic acid was added to the mixture for neutralization and the oily product thus-separated was recovered, crystallized from acetonitrile, and recrystallized from ethanol, to obtain 16.4 g (38% yield) of Coupler Monomer (7). Melting point: 227°–230° C.

| Elemental Analysis for $C_{23}H_{17}N_6O_3Cl_3$ | | | | |
|---|---|---|---|---|
| | H | C | N | Cl |
| Calc'd (%): | 3.22 | 51.93 | 15.80 | 20.02 |
| Found (%): | 3.20 | 51.78 | 15.47 | 20.32 |

SYNTHESIS EXAMPLE 2

Synthesis of 1-(2,4,6-trichlorophenyl)-3-(3-acrylamidobenzamido)-4-pyrazolyl-5-oxo-2-pyrazoline [Coupler Monomer (6)]

22 g (0.044 1 mol) of 1-(2,4,6-trichlorophenyl)-3-(3-aminobenzamido)-4-pyrazolyl-5-oxo-2-pyrazoline described in Synthesis Example 1 was dissolved in 1 liter of tetrahydrofuran and to which were added 8.8 ml (0.11 mol) of pyridine and 1 ml of nitrobenzene. To the mixture was added dropwise 12 g (0.11 mol) of acryloyl chloride while cooling with ice and the mixture was additionally stirred for about 30 minutes. After adding 500 ml of water, the mixture was extracted with ethyl acetate, and the extracted solution was dried with anhydrous sodium sulfate. After distilling off the solvent at from 20° C. to 30° C. under reduced pressure, the residual oily product was dissolved in 100 ml of ethanol, to which was then added an aqueous solution containing 2.4 g (0.06 mol) of sodium hydroxide dissolved in 50 ml of water at room temperature. After stirring for 30 minutes, 2.5 ml of acetic acid was added to the mixture for neutralization and the oily product thus-separated was crystallized from acetonitrile and recrystallized from a solvent mixture of ethanol and ethyl acetate to obtain 4.5 g (20% yield) of Coupler Monomer (6). Melting point: 206°–209° C.

| Elemental Analysis for $C_{22}H_{15}N_6O_3Cl_3$ | | | | |
|---|---|---|---|---|
| | H | C | N | Cl |
| Calc'd (%): | 2.92 | 51.02 | 16.23 | 20.56 |
| Found (%): | 2.91 | 50.87 | 16.04 | 20.26 |

SYNTHESIS EXAMPLE 3

Synthesis of 1-(2,4,6-trichlorophenyl)-3-acrylamido-4-pyrazolyl-5-oxo-2-pyrazoline [Coupler Monomer (1)]:

54.5 g (0.17 mol) of 1-(2,4,6-trichlorophenyl)-3-acetylamino-5-oxo-2-pyrazoline was dissolved in 300 ml of acetic acid, to which there was then gradually added dropwise 27.2 g (0.17 mol) of bromine. After stirring for 1 hour, the reaction mixture was poured into 900 ml of water and the crystals thus-separated were collected by filtration to obtain 57 g (84% yield) of 1-(2,4,6-trichlorophenyl)-3-acetylamino-4-bromo-5-oxo-2-pyrazoline.

57 g (0.15 mol) of the 4-bromo compound thus-synthesized and 41 g (0.6 mol) of pyrazole were well mixed and reacted by heating at 75° C. under a nitrogen gas atmosphere for 6 hours. After cooling to room temperature, the reaction mixture dissolved in ethyl acetate, washed three times with water, and dried with anhydrous sodium sulfate. The solvent was distilled off under reduced pressure and 200 cc of acetonitrile was added to the residual oily product. The crystals thus-separated were collected by filtration to obtain 20.1 g (34.7% yield) of 1-(2,4,6-trichlorophenyl)-3-acetylamino-4-pyrazolyl-5-oxo-2-pyrazoline.

31 g (0.08 mol) of the 4-pyrazolyl compound thus-synthesized was refluxed by heating in 600 ml of ethanol and to which was added 55 ml of concentrated hydrochloric acid. After cooling to about 10° C., a solution containing 39 g of potassium hydroxide dissolved in 400 ml of methanol was added thereto to neutralize the reaction solution, and the resulting solution was poured into 2.5 liters of water. The crystals thus-separated were collected by filtration to obtain 21.6 g (78% yield) of 3-amino-1-(2,4,6-trichlorophenyl)-4-pyrazolyl-5-oxo-2-pyrazoline.

Then, 17 g (0.05 mol) of the amino compound thus-synthesized was dissolved in 300 ml of tetrahydrofuran, to which were then added 10 ml (0.13 mol) of pyridine and 1 ml of nitrobenzene. To the mixture was added dropwise 13.1 g (0.12 mol) of acryloyl chloride under cooling with ice and the mixture was stirred for 1.5 hours. After adding 500 ml of water, the mixture was extracted with ethyl acetate and the extract was dried with anhydrous sodium sulfate. After distilling off the solvent under reduced pressure, the residual oily product was dissolved in 150 ml of ethanol, to which was then added an aqueous solution containing 3.0 g (0.074 mol) of sodium hydroxide dissolved in 60 ml of water at room temperature. After stirring for 30 minutes, 3 ml of acetic acid was added to the mixture for neutralization, and the oily product thus-separated was extracted with ethyl acetate, dried with anhydrous sodium sulfate, and the solvent was distilled off under reduced pressure. The residual oily product was separated and purified using silica gel column chromatography, to obtain 6.4 g (32% yield) of Coupler Monomer (1). Melting point: 151°–154° C.

| Elemental Analysis for $C_{15}H_{10}N_5O_2Cl_3$ | | | |
|---|---|---|---|
| | H | C | N | Cl |
| Calc'd (%): | H | C | N | 26.66 |
| Found (%): | 2.48 | 45.01 | 17.49 | 26.30 |

B. Polymer Compounds

SYNTHESIS EXAMPLE 4

Copolymer latex of 1-(2,4,6-trichlorophenyl)-3-(3-acrylamidobenzamido)-4-pyrazolyl-5-oxo-2-pyrazoline [Coupler Monomer (6)] and n-butyl acrylate [Latex Coupler (A)]:

A solution containing 1.25 g of sodium salt of oleyl methyl tauride dissolved in 600 ml of distilled water was stirred and heated to 95° C. while gradually introducing nitrogen gas through the solution. To the mixture was added 5 ml of an aqueous solution containing 175 mg of potassium persulfate dissolved. 20 g of n-butyl acrylate and 5 g of Coupler Monomer (6) were dissolved by heating in 200 ml of a solvent mixture of ethanol and acetonitrile and the resulting solution was added to the above-described aqueous solution at an interval of about 30 seconds while preventing the deposition of crystals. After the completion of the addition, the mixture was heated at from 85° C. to 95° C. with stirring for 45 minutes, to which was then added 3 ml of an aqueous solution containing 75 mg of potassium persulfate dissolved. After being reacted for 1 hour, the n-butyl acrylate not reacted was distilled off as an azeotropic mixture with water. The latex thus-formed was cooled, pH of which was adjusted to 6.0 with a 1 N sodium hydroxide solution and filtered. The concentration of the polymer in the latex was 14.9% and it was found that the copolymer synthesized contained 19.3% of 1-(2,4,6-trichlorophenyl)-3-(3-acrylamidobenzamido)-4-pyrazolyl-5-oxo-2-pyrazoline as the result of nitrogen analysis.

SYNTHESIS EXAMPLE 5

Copolymer latex of 1-(2,4,6-trichlorophenyl)-3-(3-methacrylamidobenzamido)-4-pyrazolyl-5-oxo-2-pyrazoline [Coupler Monomer (7)] and n-butyl acrylate [Latex Polymer (B)]:

A solution containing 1.25 g of sodium salt of oleyl methyl tauride dissolved in 600 ml of distilled water was stirred and heated to 95° C. while gradually introducing nitrogen gas through the solution. To the mixture was added 5 ml of an aqueous solution containing 175 mg of potassium persulfate dissolved. 20 g of n-butyl acrylate and 5 g of Coupler Monomer (7) were dissolved by heating in 200 ml of a solvent mixture of ethanol and acetonitrile and the resulting solution was added to the above-described aqueous solution at an interval of about 30 seconds while preventing the deposition of crystals. After the completion of the addition, the mixture was heated at from 85° C. to 95° C. with stirring for 45 minutes, to which was then added 3 ml of an aqueous solution containing 75 mg of potassium persulfate dissolved. After being reacted for 1 hour, n-butyl acrylate not reacted was distilled off as an azeotropic mixture with water. The latex thus-formed was cooled, pH of which was adjusted to 6.0 with a 1 N sodium hydroxide solution and filtered. A concentration of the polymer in the latex was 13.7% and it was found that the copolymer synthesized contained 18.4% of 1-(2,4,6-trichlorophenyl)-3-(3-methacrylamidobenzamido)-4-pyrazolyl-5-oxo-2-pyrazoline as the result of nitrogen analysis.

SYNTHESIS EXAMPLES 6 TO 20

Using the above-described coupler monomers, the polymers described below were synthesized in the same general manner as described for the copolymer in Synthesis Examples 4 and 5.

| Latex Coupler | Synthesis Example | Coupler Monomer | Amount (g) | Comonomer | Amount (g) | Polymer Concentration in Latex (wt %) | Coupler Monomer Unit in Polymer (wt %) |
|---|---|---|---|---|---|---|---|
| (C) | 6 | (6) | 5 | Butyl Acrylate | 10 | 12.3 | 29.5 |
| (D) | 7 | " | " | Ethyl Acrylate | 20 | 13.3 | 19.1 |
| (E) | 8 | " | " | Hexyl Acrylate | 20 | 15.9 | 19.6 |
| (F) | 9 | " | " | Octyl Acrylate | 20 | 14.7 | 19.5 |
| (G) | 10 | " | " | Styrene | 20 | 15.4 | 19.7 |
| (H) | 11 | (3) | 5 | Butyl Acrylte | 20 | 15.4 | 19.8 |
| (I) | 12 | " | " | " | 5 | 4.7 | 50.4 |
| (J) | 13 | (4) | 5 | " | 5 | 4.2 | 51.3 |
| (K) | 14 | (10) | 5 | Propyl Acrylate | 11.7 | 10.5 | 27.5 |
| (L) | 15 | (17) | 5 | " | 11.7 | 11.1 | 28.5 |
| (M) | 16 | (8) | 5 | Butyl Methacrylate | 5 | 5.3 | 47.3 |
| (N) | 17 | (18) | 5 | " | 5 | 4.7 | 46.5 |

-continued

| Latex Coupler | Synthesis Example | Coupler Monomer | Amount (g) | Comonomer | Amount (g) | Polymer Concentration in Latex (wt %) | Coupler Monomer Unit in Polymer (wt %) |
|---|---|---|---|---|---|---|---|
| (O) | 18 | (19) | 5 | " | 20 | 14.3 | 18.9 |
| (P) | 19 | " | " | " | 5 | 4.7 | 49.2 |
| (Q) | 20 | " | " | Ethyl Acrylate | 20 | 15.4 | 18.5 |

The 2-equivalent magenta polymer coupler latexes according to the present invention can be used individually or as mixtures of two or more thereof.

The 2-equivalent magenta polymer coupler latexes according to the present invention can also be used together with a 4-equivalent magenta polymer coupler latex, such as those described in U.S. Pat. No. 4,080,211, British Pat. No. 1,247,688, etc.

Further, a dispersion which is prepared by dispersing a hydrophobic magenta color forming coupler, for example, a magenta coupler, as described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, etc., in a hydrophilic colloid in a manner as described, for example, in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the 2-equivalent magenta polymer coupler latex according to the present invention in a manner as described in Japanese Patent Application (OPI) No. 39853/76, etc., and the resulting latex can be used, or the above-described hydrophobic magenta coupler is loaded into the 2-equivalent magenta polymer coupler latex in a manner as described in Japanese Patent Application (OPI) Nos. 59942/76 and 32552/79, U.S. Pat. No. 4,199,363, etc., and the resulting latex can be used. The term "load" used herein refers to the state in which a hydrophobic magenta coupler is incorporated into the interior of a 2-equivalent magenta polymer coupler latex, or a state in which a hydrophobic magenta coupler is deposited on the surface of a 2-equivalent magenta polymer coupler latex.

In order to satisfy the characteristics required of the photographic light-sensitive material, a dispersion which is prepared by dispersing a development inhibitor releasing (DIR) coupler as described, for example, in U.S. Pat. Nos. 3,148,062, 3,227,554, 3,733,201, 3,617,291, 3,703,375, 3,615,506, 3,265,506, 3,620,745, 3,632,345, 3,869,291, 3,642,485, 3,770,436 and 3,808,945, British Pat. Nos. 1,201,110 and 1,236,767, etc., in a hydrophilic colloid in a manner as described in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the 2-equivalent magenta polymer coupler latex according to the present invention in a manner as described in Japanese Patent Application (OPI) No. 39853/76, etc., and the resulting latex can then be used, or the above-described DIR coupler is loaded into the 2-equivalent magenta polymer coupler latex in a manner as described in Japanese Patent Application (OPI) Nos. 59942/76 and 32552/79, U.S. Pat. No. 4,199,363, etc., and the resulting latex can then be used.

Furthermore, the 2-equivalent magenta polymer coupler latex according to the present invention can be used together with a DIR compound as described, for example, in West German Patent Application (OLS) Nos. 2,529,350, 2,448,063 and 2,610,546, U.S. Pat. Nos. 3,928,041, 3,958,993, 3,961,959, 4,049,455, 4,052,213, 3,379,529, 3,043,690, 3,364,022, 3,297,445 and 3,287,129, etc.

Moreover, the 2-equivalent magenta polymer coupler latex according to the present invention can be used in combination with (1) a colored magenta coupler as described, for example, in U.S. Pat. No. 2,449,966, West German Pat. No. 2,024,186, Japanese Patent Application (OPI) Nos. 123625/74, 131448/74 and 42121/77, etc., (2) a competing coupling as described, for example, in U.S. Pat. Nos. 3,876,428, 3,580,722, 2,998,314, 2,808,329, 2,742,832 and 2,687,793, etc., (3) a stain preventing agent as described, for example, in U.S. Pat. Nos. 2,336,327, 2,728,659, 2,336,327, 2,403,721, 2,701,197 and 3,700,453, etc., (4) a dye image stabilizing agent as described, for example, in British Pat. No. 1,326,889, U.S. Pat. Nos. 3,432,300, 3,698,909, 3,574,627, 3,573,050 and 3,764,337, etc., or the like.

The color photographic light-sensitive material produced according to the present invention can also contain conventional coupler(s) other than a magenta color forming coupler. A non-diffusible coupler which contains a hydrophobic group, called a ballast group, in the molecule thereof is preferred as a coupler. A coupler can have either a 4-equivalent or a 2-equivalent property with respect to the silver ion. In addition, a colored coupler providing a color correction effect, or a coupler which releases a development inhibitor upon development can also be present therein. Furthermore, a coupler which provides a colorless product upon coupling can be employed.

A known open chain ketomethylene type coupler can be used as a yellow color forming coupler. Of these couplers, benzoyl acetanilide type and pivaloyl acetanilide type compounds are especially effective. Specific examples of yellow color forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76 and 87650/75, etc.

A phenol type compound, a naphthol type compound, etc., can be employed as a cyan color forming coupler. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 73050/80, etc.

Two or more kinds of the couplers described above can be incorporated into the same layer, or the same coupler compound can also be present in two or more layers.

A known method, for example, the method described in U.S. Pat. No. 2,322,027, can be used in order to incorporate the couplers described above into a silver halide emulsion layer. The coupler is dispersed in a hydrophilic colloid and then mixed with a silver halide emulsion. When a coupler having an acid group such as a carboxylic acid group, a sulfonic acid group, etc., is used, it can be incorporated into a hydrophilic colloid as an alkaline aqueous solution thereof.

The silver halide emulsions which can be used in the present invention are those wherein silver chloride, silver bromide, or a mixed silver halide such as silver chlorobromide, silver iodobromide, or silver chloroiodobromide is finely dispersed in a hydrophilic polymer such as gelatin. The silver halide can be chosen depending on the intended use of the photographic light-sensitive material from dispersions having a uniform grain size or those having a wide grain size distribution or from dispersions having an average grain size of from about 0.1 micron to 3 microns. These silver halide emulsions can be prepared, for example, by a single jet method, by a double jet method or a controlled double jet method, or by a ripening method such as an ammonia method, a neutral method, or an acid method. Also, these silver halide emulsions can be subjected to chemical sensitization such as a sulfur sensitization, a gold sensitization, a reduction sensitization, etc., and can contain a speed increasing agent such as a polyoxyethylene compound, an onium compound, etc. Further, a silver halide emulsion of the type wherein latent images are predominantly formed on the surface of the grains or of the type where latent images are predominantly formed inside the grains can be used in the present invention. Also, two or more kinds of silver halide photographic emulsions prepared separately and then mixed can be employed.

As a hydrophilic high molecular weight substance composed of the photographic light-sensitive layer of the present invention, a protein such as gelatin, etc., a high molecular weight non-electrolyte such as polyvinyl alcohol, polyvinyl pyrrolidone, polyacrylamide, etc., an acidic polymer such as an alginate, a polyacrylic acid salt, etc., a high molecular weight ampholite such as a polyacrylamide treated by the Hoffman rearrangement reaction, a copolymer of acrylic acid and N-vinylimidazole, etc., a cross-linking polymer as described in U.S. Pat. No. 4,215,195, and the like are suitable. Furthermore, a hydrophobic polymer dispersion such as a latex of polybutyl acrylate, etc., can be included in the continuous phase of such a hydrophilic high molecular weight substance.

The silver halide emulsion used in the present invention can be chemically sensitized, as noted above, using conventional methods. Examples of suitable chemical sensitizers include, for example, gold compounds such as chloroaurates and gold trichloride as described in U.S. Pat. Nos. 2,399,083, 2,540,085, 2,597,856, and 2,597,915; salts of a noble metal, such as platinum, palladium, iridium, rhodium and ruthenium, as described in U.S. Pat. Nos. 2,448,060, 2,540,086, 2,566,245, 2,566,263 and 2,598,079; sulfur compounds capable of forming silver sulfide by reacting with a silver salt, such as those described in U.S. Pat. Nos. 1,574,944, 2,410,689, 3,189,458 and 3,501,313; stannous salts, amines, and other reducing compounds such as those described in U.S. Pat. Nos. 2,487,850, 2,518,698, 2,521,925, 2,521,926, 2,694,637, 2,983,610 and 3,201,254 and the like.

Various compounds can be added to the photographic emulsions used in the present invention in order to prevent a reduction of the sensitivity or a formation of fog during preparation, storage, or processing. A wide variety of such compounds are known, such as heterocyclic compounds, mercury-containing compounds, mercapto compounds or metal salts, including 4-hydroxy-6-methyl-1,3,3a,7-tetraazaindene, 3-methylbenzothiazole and 1-phenyl-5-mercaptotetrazole. Other examples of such compounds which can be used are described, for example, in U.S. Pat. Nos. 1,758,576, 2,110,178, 2,131,038, 2,173,628, 2,697,040, 2,304,962, 2,324,123, 2,394,198, 2,444,605-8, 2,566,245, 2,694,716, 2,697,099, 2,708,162, 2,728,663-5, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668 and 3,622,339, British Pat. Nos. 893,428, 403,789, 1,173,609 and 1,200,188, as well as in K. Mees, *The Theory of the Photographic Process*, 3rd Ed. (1966) and the literature references cited therein.

The photographic emulsion used in the present invention can also contain one or more surface active agents. These surface active agents are commonly used as a coating aid. However, in some cases they are used as an emulsifier, a dispersant, a sensitizer, an anti-static agent, or an adhesion preventing agent.

The surface active agents can be classified into various groups, as follows: natural surface active agents such as saponin; nonionic surface active agents such as alkylene oxides, glycerols and glycidols; cationic surface active agents such as higher alkylamines, quaternary ammonium salts, heterocyclic compounds such as pyridine and the like, phosphoniums or sulfoniums; anionic surface active agents containing an acid group such as a carboxylic acid group, a sulfonic acid group, a phosphoric acid group, a sulfuric acid ester group, or phosphoric acid ester group; amphoteric surface active agents such as aminoacids, aminosulfonic acids, aminoalcohol sulfuric acid esters or aminoalcohol phosphoric acid esters. Some examples of those surface active agents which can be used are described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,971, West German Patent Application (OLS) No. 1,942,665, British Pat. Nos. 1,077,317 and 1,198,450, as well as Ryohei Oda et al., *Kaimenkasseizai no Gosei to sono Oyo (Synthesis and Application of Surface Active Agents)*, Maki Shoten (1964), A. W. Perry, *Surface Active Agents*, Interscience Publications, Inc. (1958) and J. P. Sisley, *Encyclopedia of Surface Active Agents*, Vol. II, Chemical Publishing Co. (1964).

The photographic emulsions can be spectrally sensitized, or supersensitized, using a cyanine-type dye, such as a cyanine, merocyanine, carbocyanine, etc., individually, in combinations, or in combination with a styryl dye.

These spectral sensitization techniques are well known, and are described, for example, in U.S. Pat. Nos. 2,688,545, 2,912,329, 3,397,060, 3,615,635 and 3,628,964, British Pat. Nos. 1,195,302, 1,242,588 and 1,293,862, West German Patent Application (OLS) Nos. 2,030,326 and 2,121,780, Japanese Patent Publication Nos. 4936/68 and 14030/69, etc. The sensitizers can be selected as desired depending on the purposes and use of the photographic materials to be sensitized.

The hydrophilic colloid layer, and in particular a gelatin layer in the photographic light-sensitive material used in the present invention, can be hardened using various kinds of cross-linking agents. For instance, an inorganic compound such as a chromium salt and a zirconium salt, or an aldehyde type cross-linking agent such as mucochloric acid, or 2-phenoxy-3-chloromalealdehydic acid as described in Japanese Patent Publication No. 1872/71 can be effectively used in the present invention, but non-aldehyde type cross-linking agents such as compounds having plural epoxy rings as described in Japanese Patent Publication No. 7133/59, the poly(1-aziridinyl) compounds as described in Japanese Patent Publication No. 8790/62, the active halogen compounds as described in U.S. Pat. Nos. 3,362,827 and 3,325,287 and the vinyl sulfone compounds as described in U.S. Pat. Nos. 2,994,611 and 3,582,322, Belgian Pat. No. 686,440, etc., are particularly suitable for use in the photographic light-sensitive material of the present invention.

The silver halide photographic emulsion of the present invention is suitably applied to a support. Illustrative supports include rigid materials such as glass, metal and ceramics, and flexible materials and the type of support chosen depends on the end-use objects. Typical examples of flexible supports include a cellulose nitrate film, a cellulose acetate film, a polyvinyl acetal film, a polystyrene film, a polyethylene terephthalate film, a polycarbonate film and a laminate thereof, a baryta coated paper, a paper coated with an $\alpha$-olefin polymer, suc as polyethylene, polypropylene and an ethylene-butene copolymer, a plastic film having a roughened surface as described in Japanese Patent Publication No. 19068/72, and the like. Depending upon the end-use objects of the photographic light-sensitive material, the support can be transparent, colored by adding a dye or pigment, opaque by adding, for example, titanium white, or light-shielding by adding, for example, carbon black.

The layer of the photographic light-sensitive material can be coated on a support using various coating methods, including a dip coating method, an air-knife coating method, a curtain coating method, an extrusion coating method using a hopper as described in U.S. Pat. No. 2,681,294. Also two or more layers can be coated simultaneously, using methods as described in U.S. Pat. Nos. 2,761,791, 3,508,947, 2,941,898, 3,526,528, etc.

The present invention is applicable to not only the so-called multilayer type photographic light-sensitive material comprising a support having superimposed thereon emulsion layers, each of which is sensitive to radiation of a substantially different wavelength region and forms color images of a substantially different hue, but also the so-called mixed-packet type photographic light-sensitive material comprising a support having coated thereon a layer containing packets which are sensitive to radiation of substantially different wavelength regions and form color images of a substantially different hue. The present invention can be applied to a color negative film, a color positive film, a color reversal film, a color printing paper, a color reversal printing paper, and the like.

The color photographic light-sensitive material of the present invention is, after exposure, subjected to a development processing to form dye images. Development processing includes basically a color development step, a bleaching step and a fixing step. Each step can be carried out individually or two or more steps can be combined as one step where a processing solution having two or more functions is used. Also, each step can be separated into two or more steps. The development processing can further include a pre-hardening step, a neutralization step, a first development (black-and-white development) step, a stabilizing step, a water washing step, and the like, if desired. The temperature of processing can be varied depending on the photographic light-sensitive material, the processing method, and the like. In general, the processing steps are carried out at a temperature from 18° C. to 60° C. These steps need not necessarily be conducted at the same temperature.

A color developer solution is an alkaline solution having a pH of more than 8, preferably from 9 to 12, and containing, as a developing agent, a compound whose oxidation product is capable of forming a colored compound when reacted with a color forming agent, i.e., a color coupler. The developing agent described above includes a compound capable of developing an exposed silver halide and having a primary amino group on an aromatic ring, and a precursor which forms such compound. Typical examples of preferred developing agents are, for example, 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 4-amino-3-methyl-N-ethyl-N-$\beta$-methanesulfonamidoethylaniline, 4-amino-N,N-dimethylaniline, 4-amino-3-methoxy-N,N-diethylaniline, 4-amino-3-methyl-N-ethyl-N-$\beta$-ethoxyethylaniline, 4-amino-3-methoxy-N-ethyl-N-$\beta$-methoxyethylaniline, 4-amino-3-$\beta$-methanesulfonamidoethyl-N,N-diethylaniline, and the salts thereof (for example, the sulfates, the hydrochlorides, the sulfites, the p-toluene sulfonates, and the like). Other developing agents such as those described in U.S. Pat. Nos. 2,193,015 and 2,592,364, Japanese Patent Application (OPI) No. 64933/73, L. F. A. Mason, *Photographic Processing Chemistry*, pages 226–229, Focal Press, London (1966), T. H. James, *The Theory of the Photographic Process*, 4th Edition, pages 315–320, Macmillan, New York (1977), etc., can be used. Further, an aminophenol as described in T. H. James, *The Theory of the Photographic Process*, 4th Edition, pages 311–315, etc., can be used. Also, a 3-pyrazolidone auxiliary developing agent can be used together with these developing agents.

The color developer solution can optionally contain various additives. Typical examples of such additives include alkaline agents (for example, alkali metal or ammonium hydroxides, carbonates or phosphates); pH-adjusting agents or buffers (for example, weak acids such as acetic acid, boric acid, etc., weak bases, or salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides; alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing such as those described in U.S. Pat. Nos. 3,113,864, 3,342,596, 3,295,976, 3,615,522 and 3,597,199; thiosulfonyl compounds such as those described in British Pat. No. 972,211; phenazine-N-oxides such as those described in Japanese Patent Publication No. 41675/71; those described in *Kagaku Shashin Binran (Manual of Scientific Photography)*, Vol. II, pages 29–47, and the like); stain or sludge preventing agents such as those described in U.S. Pat. Nos. 3,161,513 and 3,161,514, and British Pat. Nos. 1,030,442, 1,144,481 and 1,251,558; interlayer-effect accelerators disclosed in U.S. Pat. No. 3,536,487; preservatives (for example, sulfites, bisulfites, hydroxyamine hydrochloride, formsulfite, alkanolaminesulfite adducts, etc.) and the like.

The color photographic light-sensitive material of the present invention can be treated with various solutions prior to color development.

In the case of color reversal films, treatment with a first development solution is also carried out prior to the color development. As the first development solution, an alkaline aqueous solution containing at least one developing agent, such as hydroquinone, 1-phenyl-3-pyrazolidone, N-methyl-p-aminophenol and the like can be employed. The solution can also contain inorganic salts such as sodium sulfate; pH-adjusting agents or buffers such as borax, boric acid, sodium hydroxide and sodium carbonate; development fog inhibitors such as alkali metal halides (such as potassium bromide, etc.), and the like.

The additives illustrated above and the amounts thereof employed are well known in the color processing field.

After color development, the color photographic materials are usually bleached and fixed. The processes can be effected in a blix bath which combines the bleaching and fixing steps. Various compounds can be used as a bleaching agent, for example, ferricyanides, dichromates; water-soluble iron (III) salts, water-soluble cobalt (III) salts; water-soluble copper (II) salts; water-soluble quinones; nitrosophenols; complex salts of a polyvalent cation such as iron (III), cobalt (III), copper (II), etc., and an organic acid, for example, metal complex of an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and copper complex salt of 2,6-dipicolinic acid; peracids such as alkylperacids, persulfates, permanganates and hydrogen peroxide; hypochlorites; chlorine, bromine; bleaching powder; and the like. These can be suitably used, individually or in combination. To the bleaching solution, bleaching accelerators such as those described in U.S. Pat. Nos. 3,042,520 and 3,241,966, Japanese Patent Publication Nos. 8506/70 and 8836/70 and various other additives can be added.

Any known fixing solution can be used for fixing the photographic materials of the present invention. That is, ammonium, sodium, or potassium thiosulfate can be used as a fixing agent at a concentration of about 50 to about 200 g/liter. Fixing solutions can further contain stabilizers such as sulfites and metabisulfites; hardeners such as potassium alum; pH buffers such as acetates and borates, and the like. The fixing solution generally has a pH of more than 3 or less.

Bleaching baths, fixing baths and blixing baths as described, for example, in U.S. Pat. No. 3,582,322, Japanese Patent Application (OPI) No. 101934/73, West German Pat. No. 1,051,117 can also be employed.

The present invention will be explained in greater detail with reference to the following examples, but the present invention should not be construed as being limited thereto.

EXAMPLE 1

30 ml of an aqueous solution containing $5.6 \times 10^{-3}$ mole of each of the 2-equivalent magenta polymer coupler latexes (A) and (B) (described in Synthesis Examples 4 and 5, respectively) according to the present invention and comparative 4-equivalent magenta polymer coupler latexes (I) and (II) (described below) was mixed with 100 g of a silver halide emulsion containing $5.6 \times 10^{-2}$ mol of silver iodobromide and 8 g of gelatin, and to the mixture was added 8 ml of a 4% acetone solution of 2-hydroxy-4,6-dichloro-s-triazine sodium salt. After adjusting the pH to 6.5, the emulsion was coated on a cellulose triacetate support having a subbing layer to prepare Samples 1 to 4.

These films were exposed stepwise for sensitometry and then subjected to the following color development processing.

| | Color Development Processing Step | Time | Temperature (°C.) |
|---|---|---|---|
| 1. | Color development | 3 min 15 sec | 38 |
| 2. | Bleaching | 6 min 30 sec | " |
| 3. | Washing with water | 2 min | " |
| 4. | Fixing | 4 min | " |
| 5. | Washing with water | 4 min | " |
| 6. | Stabilizing bath | 1 min | " |

The processing solutions used in the color development processing had the following compositions:

| Color Developer Solution | |
|---|---|
| Water | 800 ml |
| 4-(N—Ethyl-N—hydroxyethyl)amino-2- | 5 g |
| Sodium Sulfite | 5 g |
| Hydroxylamine Sulfate | 2 g |
| Potassium Carbonate | 30 g |
| Potassium Hydrogen Carbonate | 1.2 g |
| Potassium Bromide | 1.2 g |
| Sodium Chloride | 0.2 g |
| Trisodium Nitrilotriacetate | 1.2 g |
| Water to make | 1 l |
| | (pH 10.1) |
| Bleaching Solution | |
| Water | 800 ml |
| Iron (III) Ammonium Ethylenediamine-tetraacetate | 100 g |
| Disodium Ethylenediaminetetraacetate | 10 g |
| Potassium Bromide | 150 g |
| Acetic Acid | 10 g |
| Water to make | 1 l |
| | (pH 6.0) |
| Fixing Solution | |
| Water | 800 ml |

| | -continued | |
|---|---|---|
| Ammonium Sulfite | | 10 g |
| Sodium Hydrogen Sulfite | | 2.5 g |
| Water to make | | 1 l |
| | | (pH 6.0) |
| Stabilizing Bath | | |
| Water | | 800 ml |
| Formalin (37% formaldehyde) | | 5 ml |
| Drywell | | 3 ml |
| Water to make | | 1 l |

The photographic properties thus-obtained are shown in Table 1 below.

TABLE 1

| | Photographic Properties | | | |
|---|---|---|---|---|
| Sample | Fog | Gamma | Relative Sensitivity | Maximum Color Density |
| 1 (Present Invention) | 0.05 | 1.73 | 100 | 1.95 |
| 2 (Present Invention) | 0.04 | 1.50 | 94 | 1.83 |
| 3 (Comparison) | 0.05 | 0.75 | 63 | 0.92 |
| 4 (Comparison) | 0.05 | 0.65 | 55 | 0.85 |

It is apparent from the results shown in Table 1 that Samples 1 and 2 according to the present invention provide increased gamma, relative sensitivity, and maximum color density without an increase in fog in comparison with the Comparative Samples 3 and 4, and thus they are clearly advantageous with respect to the color forming property.

Further, Samples 1, 2, 3 and 4 described above were contacted with 0 ppm or 20 ppm of formaldehyde vapor for 24 hours under the conditions of 45° C. and 70% relative humidity and then exposed stepwise for sensitometry and subjected to the same color development processing as described above. The maximum color densities obtained under these conditions are shown in Table 2 below.

TABLE 2

| Decrease in Color Density due to Formaldehyde (ratio of decrease in maximum density) | | | |
|---|---|---|---|
| Sample | 0 ppm | 20 ppm | Ratio of Decrease |
| 1 (Present Invention) | 1.95 | 1.95 | 0 |
| 2 (Present Invention) | 1.83 | 1.81 | 1.0 |
| 3 (Comparison) | 0.92 | 0.55 | 40.0 |
| 4 (Comparison) | 0.85 | 0.40 | 53.0 |

From the results shown in Table 2, it is apparent that the 4-equivalent magenta polymer coupler latexes undergo a dramatic decrease in color density upon the contact with formalin vapor. On the contrary, decrease in color density is hardly observed with the 2-equivalent magenta polymer coupler latexes according to the present invention, which indicates that the resistance to formalin is extremely high.

The comparative 4-equivalent magenta polymer coupler latexes (I) and (II) have the following compositions.

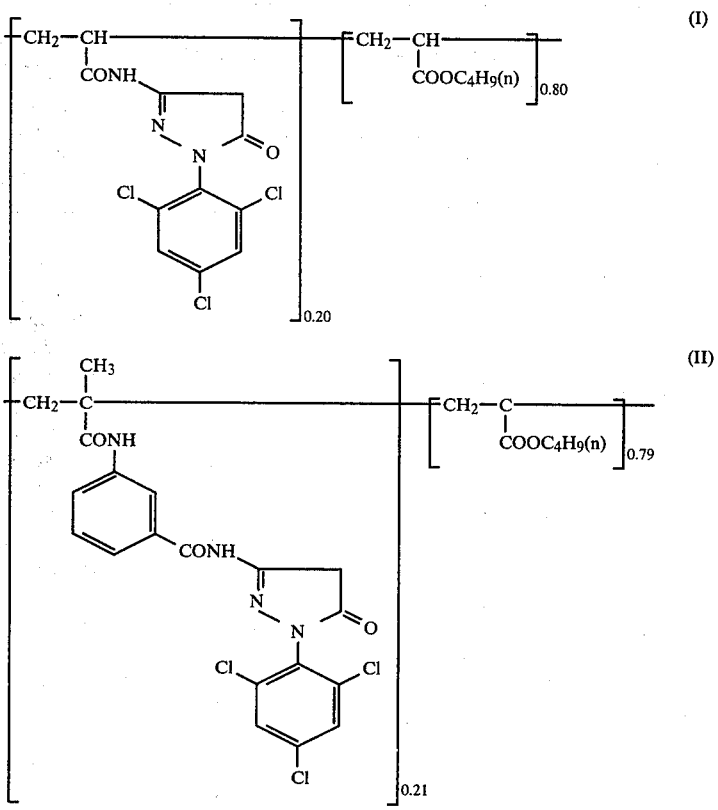

EXAMPLE 2

40 ml of an aqueous solution containing $7.5 \times 10^{-3}$ mol of each of the previously described 2-equivalent magenta polymer coupler latexes (L) and (K) according to the present invention and the comparative magenta polymer coupler latexes (III), (IV), (V), (VI), and (VII) (described below) was mixed with 100 g of a silver halide emulsion containing $8.4 \times 10^{-2}$ mol of silver iodobromide and 10 g of gelatin and to which 8 ml of a 4% acetone solution of 2-hydroxy-4,6-dichloro-s-triazine sodium salt was added. The pH of the mixture was adjusted to 6.7 and the mixture was coated on a cellulose triacetate film in an amount of silver coated of $1.2 \times 10^{-3}$ mol/m$^2$, to prepare Samples 5, 6, 7, 8, 9, 10 and 11.

These films were exposed stepwise for sensitometry and then subjected to the following color development processing.

| Color Development Processing Step (38° C.) | |
|---|---|
| | Time (min.) |
| 1. First development | 3 |
| 2. Washing with water | 1 |
| 3. Reversal | 2 |
| 4. Color development | 6 |
| 5. Control | 2 |
| 6. Bleaching | 6 |
| 7. Fixing | 4 |
| 8. Washing with water | 4 |
| 9. Stabilizing | 1 |
| 10. Drying | |

The processing solutions used in the color development processing had the following compositions:

| First Development Solution | |
|---|---|
| Water | 800 ml |
| Sodium Tetrapolyphosphate | 2.0 g |
| Sodium Hydrogen Sulfite | 8.0 g |
| Sodium Sulfite | 37.0 g |
| 1-Phenyl-3-pyrazolidone | 0.35 g |
| Hydroquinone | 5.5 g |
| Sodium Carbonate Monohydrate | 28.0 g |
| Potassium Bromide | 1.5 g |
| Potassium Iodide | 13.0 mg |
| Sodium Thiocyanate | 1.4 g |
| Water to make | 1 l |
| Reversal Solution | |
| Water | 800 ml |
| Hexasodium Nitrilo-N,N,N—trimethylene | 3.0 g |
| Stannous Chloride Dihydrate | 1.0 g |
| Sodium Hydroxide | 8.0 g |
| Glacial Acetic Acid | 15.0 ml |
| Water to make | 1 l |
| Color Development Solution | |
| Water | 800 ml |
| Sodium Tetrapolyphosphate | 2.0 g |
| Benzyl Alcohol | 5.0 ml |
| Sodium Sulphite | 7.5 g |
| Trisodium Phosphate (12 hydrate) | 36.0 g |
| Potassium Bromide | 1.0 g |
| Potassium Iodide | 90.0 mg |
| Sodium Hydroxide | 3.0 g |
| Citrazic Acid | 1.5 g |
| 4-Amino-3-methyl-N—ethyl-N—(β-hydroxyethyl)aniline Sesquisulfate Monohydrate | 11.0 g |
| Ethylenediamine | 3.0 g |
| Water to make | 1.0 l |
| Control Solution | |
| Water | 800 ml |
| Glacial Acetic Acid | 5.0 ml |
| Sodium Hydroxide | 3.0 g |
| Dimethylaminoethaneisothiourea Dihydrochloride | 1.0 g |
| Water to make | 1 l |
| Bleaching Solution | |
| Water | 800 ml |
| Sodium Ethylenediaminetetraacetate Dihydrate | 2.0 g |
| Ammonium Iron (II) Ethylenediaminetetraacetate Dihydrate | 120.0 g |
| Potassium Bromide | 100.0 g |
| Water to make | 1 l |
| Fixing Solution | |
| Water | 800 ml |
| Ammonium Thiosulfate | 80.0 g |
| Sodium Sulfite 5.0 g | |
| Sodium Hydrogen Sulfite | 5.0 g |
| Water to make | 1 l |
| Stabilizing Bath | |
| Water | 800 ml |
| Formalin (37 wt % formaldehyde) | 5.0 ml |
| Fuji Drywell | 5.0 ml |
| Water to make | 1.0 l |

The photographic properties thus-obtained are shown in Table 3 below.

TABLE 3

| Sample | Fog | Gamma | Maximum Color Density |
|---|---|---|---|
| 5 (Present Invention) | 0.04 | 1.32 | 1.95 |
| 6 (Present Invention) | 0.03 | 1.18 | 1.89 |
| 7 (Comparison) | 0.03 | 0.75 | 0.93 |
| 8 (Comparison) | 0.03 | 0.82 | 1.05 |
| 9 (Comparison) | 0.03 | 0.68 | 0.88 |
| 10 (Comparison) | 0.02 | 1.09 | 0.82 |
| 11 (Comparison) | 0.03 | 0.77 | 0.95 |

It is apparent from the results shown in Table 3 that the 2-equivalent magenta polymer coupler latexes according to the present invention have good color forming properties in comparison with the comparative magenta polymer coupler latexes.

Separate Samples 5 to 11 were exposed for sensitometry and subjected to the same development processing as described above, and then the strips thus-prepared were exposed to a day light fluorescent lamp of about 2,000 lux for 2 weeks and the durability of the magenta color image was determined. The results obtained are shown in Table 4 below.

TABLE 4

| | Color Image Fastness | |
|---|---|---|
| Sample | $D_{0.5}$* | $D_{0.8}$* |
| 5 | 0.39 | 0.60 |
| 6 | 0.38 | 0.58 |
| 7 | 0.32 | 0.42 |
| 8 | 0.29 | 0.40 |
| 9 | 0.34 | 0.48 |
| 10 | 0.25 | 0.35 |
| 11 | 0.27 | 0.38 |

*$D_{0.5}$ and $D_{0.8}$ indicate the densities before fading test 0.5 and 0.8, respectively.

From the results shown in Table 4, it is apparent that the fastness of color images to the fluorescent lamp which is obtained from the 2-equivalent magenta polymer coupler latexes according to the present invention is superior to the comparative magenta polymer coupler latexes.

The comparative magenta polymer coupler latexes (III), (IV), (V), (VI) and (VII) have the following compositions.

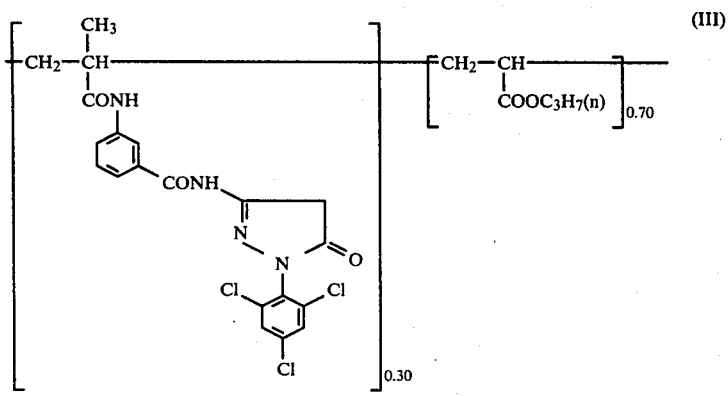
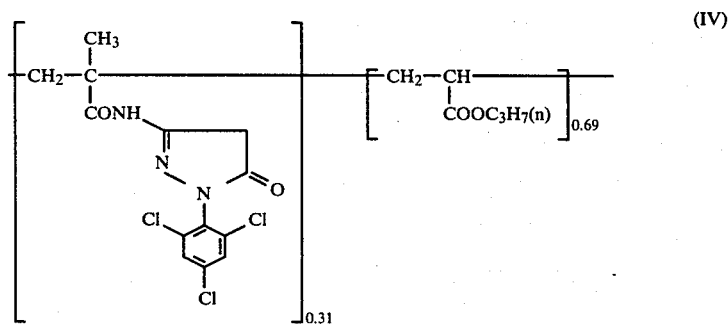
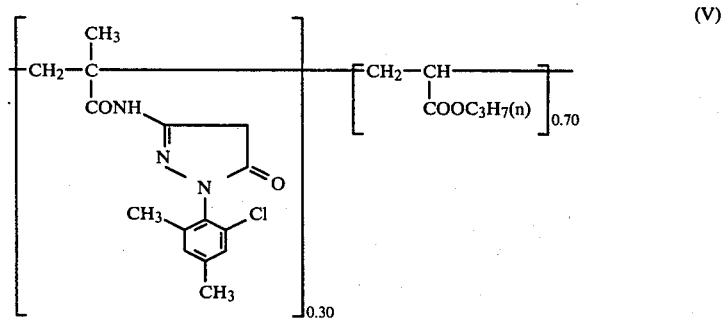
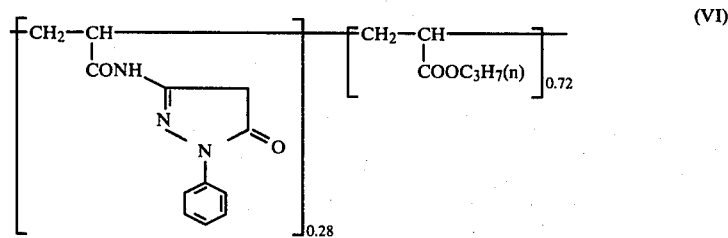
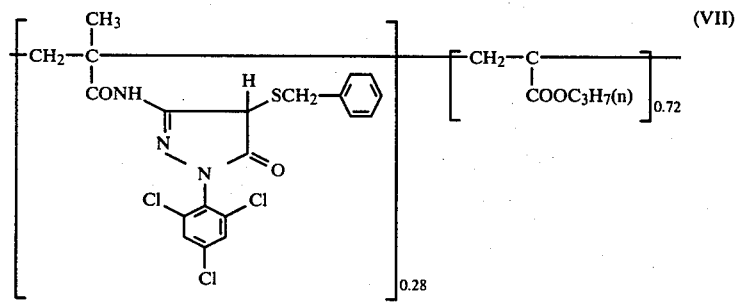

EXAMPLE 3

30 ml of an aqueous solution containing $7 \times 10^{-3}$ mol of each of the 2-equivalent magenta polymer coupler latexes (M) and (N) according to the present invention and the known 4-equivalent magenta polymer coupler latexes (VIII) and (IX) was mixed with 100 g of a silver halide emulsion containing $5 \times 10^{-2}$ mol of silver chlorobromide and 7 g of gelatin and to which 8 ml of a 4% acetone solution of 2-hydroxy-4,6-dichloro-5-triazine sodium salt was added. The pH of the mixture was adjusted to 6.7 and coated on a baryta coated paper, in an amount of silver coated of $4 \times 10^{-3}$ mol/m², to prepare Samples 12, 13, 14 and 15.

These films were exposed stepwise for sensitometry and then subjected to the following color development processing.

| Color Development Processing | Time | Temperature (°C.) |
|---|---|---|
| 1. Color development | 3 min 30 sec | 33 |
| 2. Bleach-fixing | 1 min 30 sec | 33 |
| 3. Washing with water | 2 min 30 sec | 25 to 30 |

The processing solutions used in the color development processing had the following compositions:

| Color Development Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N—ethyl-N—(β-methanesulfonamidoethyl) -m-toluidine Sesquisulfate Monohydrate | 5 g |
| Water to make | 1 l |
| | (pH 10.20) |
| Bleach-Fixing Solution | |
| Ethylenediaminetetraacetic Acid | 2 g |
| Ferric Salt of Ethylenediaminetetraacetate | 40 g |
| Sodium Sulfite | 5 g |
| Ammonium Thiosulfate | 70 g |
| Water to make | 1 l |

The photographic properties thus-obtained are shown in Table 5 below.

TABLE 5

| Sample | Fog | Gamma | Relative Sensitivity | Maximum Density |
|---|---|---|---|---|
| 12 | 0.03 | 2.15 | 100 | 3.25 |
| 13 | 0.03 | 2.11 | 97 | 3.07 |
| 14 | 0.02 | 1.75 | 83 | 2.12 |
| 15 | 0.03 | 1.83 | 86 | 2.18 |

As is apparent from the results shown in Table 5, the 2-equivalent magenta polymer coupler latexes according to the present invention clearly have good color forming properties.

Then, Samples 12, 13, 14 and 15 were continuously exposed for sensitometry and subjected to the same color development processing as described above. The strips thus-prepared were exposed to xenon light of about 100,000 lux for 3 days and the durability of the magneta color images was determined. The results thus-obtained are shown in Table 6 below.

TABLE 6

| | Color Image Fastness | | |
|---|---|---|---|
| Sample | $D_{0.5}$* | $D_{1.0}$* | $D_{2.0}$* |
| 12 | 0.18 | 0.35 | 0.70 |
| 13 | 0.22 | 0.40 | 0.75 |
| 14 | 0.11 | 0.18 | 0.23 |
| 15 | 0.14 | 0.25 | 0.42 |

*$D_{0.5}$, $D_{1.0}$ and $D_{2.0}$ indicate the densities before fading test were 0.5, 1.0 and 2.0, respectively.

From the results shown in Table 6, it is apparent that the light fastness of the color images formed from the 2-equivalent magenta polymer coupler latexes according to the present invention is excellent in comparison with that obtained from the comparative 4-equivalent magenta polymer coupler latexes.

The comparative magenta polymer coupler latexes (VIII) and (IX) have the following compositions.

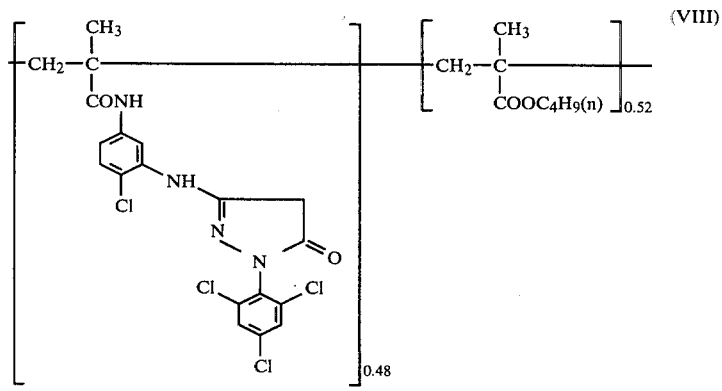

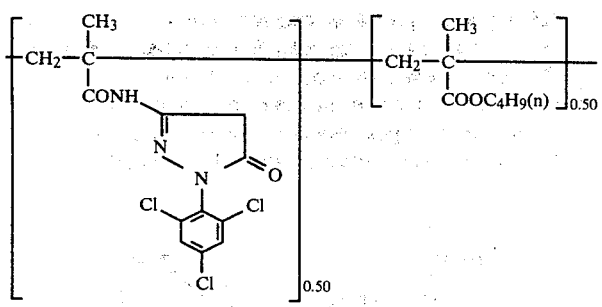

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a silver halide emulsion layer containing a 2-equivalent magenta color image forming polymer coupler latex which is capable of forming a dye upon coupling with an oxidation product of an aromatic primary amine developing agent and which is a polymer or copolymer having a repeating unit derived from a monomer represented by formula (I)

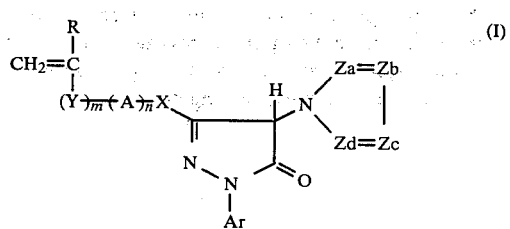

wherein R represents a hydrogen atom, a lower alkyl group containing from 1 to 4 carbon atoms, or a chlorine atom; X represents —CONH—, —NH—, —NHCONH— or —NHCOO—; Y represents —CONH— or —COO—; A represents an unsubstituted or substituted alkylene group which may be a straight chain or a branched chain, or an unsubstituted or substituted phenylene group; Ar represents an unsubstituted or substituted phenylene group; Za, Zb, Zc and Zd can each represent a methine group, a substituted methine group, or —N=; m represents 0 or 1; and n represents 0 or 1.

2. A silver halide color photographic light-sensitive material as in claim 1, wherein the alkylene group represented by A is an alkylene group having from 1 to 10 carbon atoms.

3. A silver halide color photographic light-sensitive material as in claim 1, wherein the substituent for the alkylene group or the phenylene group represented by A is an aryl group, a nitro group, a hydroxy group, a cyano group, a sulfo group, an alkoxy group, an aryloxy group, an acyloxy group, an acylamino group, a sulfonamido group, a sulfamoyl group, a halogen atom, a carboxy group, a carbamoyl group, an alkoxycarbonyl group, or a sulfonyl group.

4. A silver halide color photographic light-sensitive material as in claim 1, wherein the substituent for the phenyl group represented by Ar is an alkyl group, an alkoxy group, an aryloxy group, an alkoxycarbonyl group, an acylamino group, a carbamoyl group, an alkylcarbamoyl group, a dialkylcarbamoyl group, an arylcarbamoyl group, an alkylsulfonyl group, an arylsulfonyl group, an alkylsulfonamido group, an arylsulfonamido group, a sulfamoyl group, an alkylsulfamoyl group, a dialkylsulfamoyl group, an alkylthio group, an arylthio group, a cyano group, a nitro group, or a halogen atom.

5. A silver halide color photographic light-sensitive material as in claim 1, wherein the substituent for the phenyl group represented by Ar is a halogen atom, an alkyl group, an alkoxy group, an alkoxycarbonyl group, or a cyano group.

6. A silver halide color photographic light-sensitive material as in claim 1, wherein the substituent for a methine group represented by Za, Zb, Zc, or Zd is a straight chain or branched chain alkyl group having from 1 to 10 carbon atoms, a cycloalkyl group, an aralkyl group, an aryl group, a heterocyclic group, an alkoxycarbonyl group, an aryloxycarbonyl group, an aralkyloxycarbonyl group, an alkoxy group, an aryloxy group, an alkylthio group, a carboxy group, an acylamino group, a diacylamino group, an N-alkylacylamino group, an N-arylacylamino group, a ureido group, a thioureido group, an alkyloxycarbonylamino group, an aryloxycarbonylamino group, an anilino group, an alkylamino group, a cycloamino group, an alkylcarbonyl group, an arylcarbonyl group, a sulfonamido group, a carbamoyl group, a sulfamoyl group, a cyano group, an acyloxy group, a sulfonyloxy group, an alkylsulfonyl group, an arylsulfonyl group, a halogen atom, a sulfo group, or a nitro group.

7. A silver halide color photographic light-sensitive material as in claim 1, wherein the heterocyclic group represented by

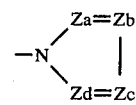

is a pyrazolyl group, an imidazolyl group, a triazolyl group, or a tetrazolyl group.

8. A silver halide color photographic light-sensitive material as in claim 1, wherein the heterocyclic group represented by

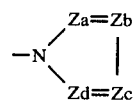

is a pyrazolyl group in which Za represents —N=, and Zb, Zc and Zd each represents a methine group or a substituted methine group.

9. A silver halide color photographic light-sensitive material as in claim 1, wherein the polymer is a homopolymer.

10. A silver halide color photographic light-sensitive material as in claim 1, wherein the polymer is a copolymer.

11. A silver halide color photographic light-sensitive material as in claim 10, wherein the copolymer contains a repeating unit derived from a non-color forming monomer which does not couple with the oxidation product of an aromatic primary amine developing agent.

12. A silver halide color photographic light-sensitive material as in claim 11, wherein the non-color forming monomer is an acrylic acid ester, an acrylic acid amide, a vinyl ester, an acrylonitrile, an aromatic vinyl compound, itaconic acid, citraconic acid, crotonic acid, vinylidene chloride, a vinyl alkyl ether, an ester of maleic acid, N-vinyl-2-pyrrolidone, N-vinyl pyridine, or 2- or 4-vinyl pyridine.

13. A silver halide color photographic light-sensitive material as in claim 1, wherein the color image forming polymer latex contains repeating units derived from a monomer represented by formula (I) in an amount of from 5% to 80% by weight.

14. A silver halide color photographic light-sensitive material as in claim 13, wherein the gram number of the polymer latex containing 1 mol of coupler monomer is from about 250 to 3,000.

15. A method of forming a color image comprising developing an imagewise exposed silver halide color photographic light-sensitive material comprising a support having thereon a silver halide emulsion layer containing a 2-equivalent magenta color image forming polymer coupler latex which is capable of forming a dye upon coupling with an oxidation product of an aromatic primary amine developing agent and which is a polymer or copolymer having a repeating unit derived from a monomer represented by formula (I)

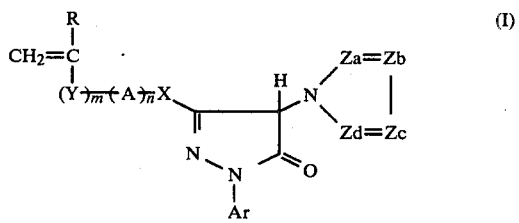

wherein R represents a hydrogen atom, a lower alkyl group containing from 1 to 4 carbon atoms or a chlorine atom; X represents —CONH—, —NH—, —NHCONH— or —NHCOO—; Y represents —CONH— or —COO—; A represents an unsubstituted or substituted alkylene group which may be a straight chain or a branched chain or an unsubstituted or substituted phenylene group; Ar represents an unsubstituted or substituted phenyl group; Za, Zb, Zc, and Zd can each represent a methine group, a substituted methine group or —N=; m represents 0 or 1; and n represents 0 or 1;

wherein said developing is conducted using an alkaline aqueous solution containing an aromatic primary amine developing agent.

* * * * *